United States Patent [19]
Squires et al.

[11] Patent Number: 6,107,035
[45] Date of Patent: Aug. 22, 2000

[54] METHOD FOR DETERMINING PREDISPOSITION TO BOAR TAINT

[75] Inventors: E James Squires, Guelph; Shawn Davis, Rockwood, both of Canada; Alan W. Steggles, Ravenna; Petra VanDerMark, Stow, both of Ohio

[73] Assignee: University of Guelph, Guelph, Canada

[21] Appl. No.: 09/041,517

[22] Filed: Mar. 13, 1998

Related U.S. Application Data

[60] Provisional application No. 60/036,585, Mar. 14, 1997.

[51] Int. Cl.⁷ .......................... C12Q 1/68; G01N 33/53; C12P 19/34; C07H 21/04
[52] U.S. Cl. ..................... 435/6; 435/7.1; 435/91.1; 435/91.2; 435/91.21; 536/23.1; 536/23.2; 536/24.3
[58] Field of Search .................. 435/6, 7.1, 7.2, 435/91.1, 91.2, 91.21; 536/23.1, 23.2, 23.5, 24.3, 24.31, 24.33

[56] References Cited

PUBLICATIONS

Ishii Ohba et al J. Biochem. vol. 95 No. 2 pp. 335–344, 1984.
Vandermark et al biochemcial and Biophysical Research Comm. vo. 240 No. 1 abstract (one page), 1997.
Ozols, J. 1989, "Structure of cytochrom b5 and its topology in the microsomal membrane", Biochimica et Biophysica Acta, 997:121–130.
Abe, K., Kimura, S., Kizawa, R., Anan, F.K., and Y. Sugita. 1985. Amino acid sequences of cytochrome b5 from human, porcine, and bovine erythrocytes and comparison with liver microsomal cytochrome b5. J. Biochem.97:1659.
Cristiano, R.J., Giordano, S.J. and A.W. Steggles. 1993. The isolation and characterization of the bovine cytochrome b5 gene, and a transcribed pseudogene. Geneomics. 17:348.
Giordano, S, Kaftory, A. and A.W. Steggles. 1994. A splicing mutation in the cytochrome b5 gene from a patient with congenital methemoglobinemia. Hum. Genet. 93:568–570.
Giordano, S.J. and Steggles, A.W. 1993. Differential expression of the MRNA's for the soluble and membrane–bound forms of rabbit cytochrome b5. Biochim. Biophys. Acta. 1172:95–100.
Hultquist, D. and Passon, P., 1971. Catalysis of methemoglobin reduction by erythrocyte cytochrome $b_5$ and cytochrome $b_5$ reductase. Nature New Biol. 229:252–254.
Hultquist, D.E., Dean, R.T., and R.H. Douglas. 1974. Homogeneous cytochrome b5 from human erythrocytes. Biochem. Biophys. Res. Comm. 60(1):28–34.
Kimura, S., Abe, K., and Y. Sugita. 1984. Differences in C–terminal amino acid sequences between erythrocyte and liver cytochrome b5 isolated from pig and human: evidence for two tissue–specific forms of cytochrome b5. FEBS lett. 169(2):143–146.
Lee–Robichaud, P., Wright, J.N., Akhtar, M.E., and M. Akhtar. 1995. Modulation of the activity of human 17,α–hydroxylase–17,20–lyase (CYP17) by cytochrome b5: endocrinological and mechanistic implications. Biochem. J., 308:901–908.
Li, X.R, Giordano, S.J., Yoo, M. and Steggles, A.W. 1995. The isolation and characterization of the human cytochrome b5 gene. Biochem. Biophys. Res. Comm., vol. 209, No. 3, pp. 894–900.
Meadus, W.J., Mason, J.I. and E.J. Squires. 1993. Cytochrome P450c17 from porcine and bovine adrenal catalyses the formation of 5,16–androstadien–3β–ol from pregnenolone in the presence of cytochrome b5. J. Steroid Biochem. Molec. Biol. 46(5):565–572.
Sakai, Y., Yanase, T., Takayanagi, R., Nako, R., Nishi, Y., Haji, M., and H. Nawata. 1993. High expressionof cytochrome b5 in adrenocortical adenomas from pateints with Cushings syndrome associated with high secretion of adrenal androgens. J. Clin. Endocrinol. Metab. 76:1286.

*Primary Examiner*—Kenneth R. Horlick
*Assistant Examiner*—Jeffrey Siew
*Attorney, Agent, or Firm*—Bereskin & Parr

[57] ABSTRACT

A method for determining if a pig is predisposed to boar taint comprising assaying for a low molecular weight isoform of cytochrome b5 in a sample from the pig.

6 Claims, 5 Drawing Sheets

FIGURE 4
A
260 bp
B
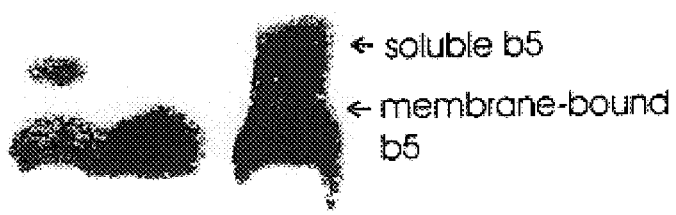
← soluble b5
← membrane-bound b5

FIGURE 5

Met Ala Glu Gln Ser Asp Lys Ala Val Lys Tyr Tyr Thr Leu Glu Glu

Ile Gln Lys His Asn Asn Ser Lys Ser Thr Trp Leu Ile Leu His His

Lys Val Tyr Asp Leu Thr Lys Phe Leu Glu Glu His Pro Gly Gly Glu

Glu Val Leu Arg Glu Gln Ala Gly Gly Asp Ala Thr Glu Asn Phe Glu

Asp Val Gly His Ser Thr Asp Ala Arg Glu Leu Ser Lys Thr Phe Ile

Ile Gly Glu Leu His Pro Asp Asp Arg Ser Lys Ile Ala Lys Pro Ser

Glu Thr Leu Ile Thr Thr Val Glu Ser Asn Ser Ser Trp Trp Thr Asn

Trp Val Ile Pro Ala Ile Ser Ala Leu Val Val Ser Leu Met Tyr His

Phe Tyr Thr Ser Glu Asn

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Porcine Cytochrome b5

(xi) SEQUENCE DESCRIPTION: SEQ ID NO:1:

```
Met Ala Glu Gln Ser Asp Lys Ala Val Lys Tyr Tyr Thr Leu Glu Glu
1               5                   10                  15

Ile Gln Lys His Asn Asn Ser Lys Ser Thr Trp Leu Ile Leu His His
            20                  25                  30

Lys Val Tyr Asp Leu Thr Lys Phe Leu Glu Glu His Pro Gly Gly Glu
        35                  40                  45

Glu Val Leu Arg Glu Gln Ala Gly Gly Asp Ala Thr Glu Asn Phe Glu
    50                  55                  60

Asp Val Gly His Ser Thr Asp Ala Arg Glu Leu Ser Lys Thr Phe Ile
65                  70                  75                  80

Ile Gly Glu Leu His Pro Asp Asp Arg Ser Lys Ile Ala Lys Pro Ser
                85                  90                  95

Glu Thr Leu Ile Thr Thr Val Glu Ser Asn Ser Ser Trp Trp Thr Asn
                100                 105                 110

Trp Val Ile Pro Ala Ile Ser Ala Leu Val Val Ser Leu Met Tyr His
            115                 120                 125

Phe Tyr Thr Ser Glu Asn
    130
```

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:2:

CTGCACCACA AAGTGTACGA                                  20

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:3:

GTAGAAGTGA TACATCAGGG A                             21

METHOD FOR DETERMINING PREDISPOSITION TO BOAR TAINT

This application claims benefit from U.S. provisional application serial No. 60/036,585 filed on Mar. 14, 1997.

FIELD OF THE INVENTION

The invention relates to a method for determining if a pig is predisposed to boar taint by assaying for a low molecular weight isoform of cytochrome b5 in a sample from the pig.

BACKGROUND OF THE INVENTION

Boar taint refers to the disagreeable, 'urine like' odor and flavor associated with heated or cooked meat of some uncastrated pigs. Affected and unaffected pigs are not readily distinguishable using commercially viable methods, young male pigs have been castrated to prevent boar taint. However, castration has significant economic drawbacks. Castrated pigs have inferior carcass characteristics and have a lower feed efficiency. It is estimated that uncastrated pigs have a 5–10% improvement in lean meat production over castrated pigs. Castrating young pigs is also cumbersome and costly. Consequently, a substantial gain in productivity can be realized by using entire male pigs for pork production (deLange, C F M and Squires, E J, 1995). Therefore, methods to prevent or determine predisposition to boar taint, that do not require castration of young pigs, are needed.

The 16-androstene steroids, primarily 5α-androst-16-en-3-one (androstenone) have been associated with boar taint (Patterson, 1968; Bonneau, 1982), and levels of the steroids in fat have been used for estimating boar taint (Squires, 1990; Squires et al., 1991). The 16-androstene steroids are produced in the Leydig cells of the testis and then pass, via the spermatic vein, into the systemic circulation (Bonneau, 1982). Due to their hydrophobic nature, 16-androstene steroids are absorbed from the circulation by the fatty tissues. Subsequent volatization of the steroids during the heating process produces the off odor and flavor associated with boar taint.

The initial reaction in the formation of the 16-androstene steroids in the testis is catalyzed by the andien-β synthase system (Katkov and Gower, 1970). Components of the andien-β synthase system are: cytochrome b5, cytochrome P450c17, NADH cytochrome b5 reductase, NADPH cytochrome P450c17 reductase.

Cytochrome P450c17 converts C21 pregnenolone to C19, 5,16-androstadien-3β-ol which is eventually converted into the pungent androstenone. Cytochrome P450c17 catalyses the formation of the androgen precursor dehydroepiandrosterone (DHEA) from pregnenolone via the C17,20-hydroxy/lyase reaction. Levels of the growth promoting androgens and, therefore, cytochrome P450c17 must remain unaltered in any attempt to reduce the levels of the 16-androstene steroids associated with boar taint.

Cytochrome b5 has been found to be important for the formation of the 16-androstene steroids in vitro (Meadus et al., 1993; Lee-Robichaud et al., 1995). High levels of cytochrome b5 have also been associated with high levels of adrenal steroidogenesis (Sakai et al., 1993). Cytochrome b5 is a small amphipathic hemeprotein which is capable of accepting and transferring a single electron (Velick and Strittmatter, 1956). Two isoforms of cytochrome b5 exist in mammals; a larger, 134 amino acid membrane-bound isoform and a smaller, 98 amino acid soluble isoform (Kimura et al., 1984; Abe et al., 1985). The soluble isoform lacks the C-terminal hydrophobic tail possessed by the membrane-bound isoform and contains only the N-terminal 98 amino acid catalytic domain whose sequence is identical to that of the membrane-bound isoform, except for the 98th amino acid which is different in the porcine isoforms (Cristiano et al., 1993).

In humans and rabbits, the soluble and microsomal isoforms of cytochrome b5 have been reported to originate from a single gene (Giordano and Steggles, 1993). Different isoforms of cytochrome b5 result from differential processing of the pre-mRNA transcript and the gene has been isolated and characterized in humans (Li et al.). Expression of the microsomal isoform has been reported to be ubiquitous, being present in all tissues examined (Giordano and Steggles, 1993). Soluble cytochrome b5 is found in erythrocytes and functions in vivo to reduce methemoglobin (Hulquist and Passon, 1971). Soluble cytochrome b5 mRNA has also been detected in lung, gall bladder, adrenal gland and bone marrow suggesting that soluble cytochrome b5 participates in other redox reactions (Giordano and Steggles, 1993). Most recently, soluble cytochrome b5 has been reported to be involved in the biosynthesis of the sialic acid, N-glycolylneuraminic acid in the liver (Kawano et al., 1994).

SUMMARY OF THE INVENTION

The present inventors have determined that there is a strong positive correlation between levels of a low molecular weight isoform of cytochrome b5 in the testis of male pigs and levels of 16-androstene steroids in fat from the pigs. In particular, pigs exhibiting fat 16-androstene steroid concentrations between 2.5 and 6 μg/g fat were found to express high levels of a low molecular weight isoform of cytochrome b5 whereas pigs exhibiting fat 16-androstene steroid concentrations between 0.2 and 1.5 μg/g fat were found to express minimal amounts of this isoform. Levels of cytochrome P450c17 and the high molecular weight isoform of cytochrome b5 were not significantly changed. Therefore, detecting the low molecular weight isoform of b5 can be used to predict the levels of 16-androstene steroids in fat which is indicative of the potential for boar taint.

Accordingly, broadly stated, the present invention relates to a method for determining if a pig is predisposed to boar taint comprising assaying for a low molecular weight isoform of cytochrome b5 in a sample from the pig. The presence of a low molecular weight isoform of b5 can be determined directly or indirectly using biochemical, immunological, and nucleic acid-based techniques.

The finding of a correlation between the low molecular weight isoform of cytochrome b5 and 16-androstene steroids in pigs indicates that a substance that affects the low molecular weight isoform of cytochrome b5 will be useful in preventing boar taint. Therefore, the present invention also relates to a method for preventing boar taint in a pig comprising administering an amount of a substance which affects a low molecular weight isoform of cytochrome b5 such that it reduces 16-androstene concentrations in the fat of the pig. Substances that can affect the low molecular weight isoform of cytochrome b5 include antibodies to the low molecular weight isoform and antisense nucleotides that are complimentary to the nucleic acid sequence of the low molecular weight isoform of cytochrome b5.

The invention also provides methods for identifying substances which directly or indirectly affect the low molecular weight isoform of cytochrome b5 and therefore are useful in the prevention of boar taint. Accordingly, the invention relates to a method of screening for a substance for use in the prevention of boar taint comprising:

(a) reacting cytochrome P450c17, and a substrate which is converted to a 16-androstene steroid in the presence of cytochrome P450c17, and a low molecular weight isoform of cytochrome b5, and at least one test substance, under conditions which permit the formation of a 16-androstene steroid;

(b) comparing the amount of 16-androstene steroid produced in (a) with an amount produced in a control reaction without the test substance;

(c) identifying a test substance which results in the formation of a lower amount of 16-androstene steroid and thereby can be used in the prevention of boar taint.

The invention still further provides a method for breeding pigs which have a lower incidence of boar taint comprising selecting pigs that express low levels of a low molecular weight isoform to cytochrome b5; and breeding the pigs. Pigs that express low levels of low molecular weight cytochrome b5 can be identified using biochemical, immunological, and nucleic acid techniques.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 4A & 4B Analysis of RT/PCR products. FIG. 4A. Agarose gel electrophoresis. FIG. 4B. Southern blot of A. Lanes 1–3 are as follows: 3-testis #135; 4-testis #238; 5-whole blood. Testis were used from #135 with androstenone level=1.711 µg/g and #238 with androstenone level= 0.725 µg/g.

FIG. 5. Shows the amino acid sequence of porcine cytochrome b5.

DETAILED DESCRIPTION OF THE INVENTION

Figure 1:
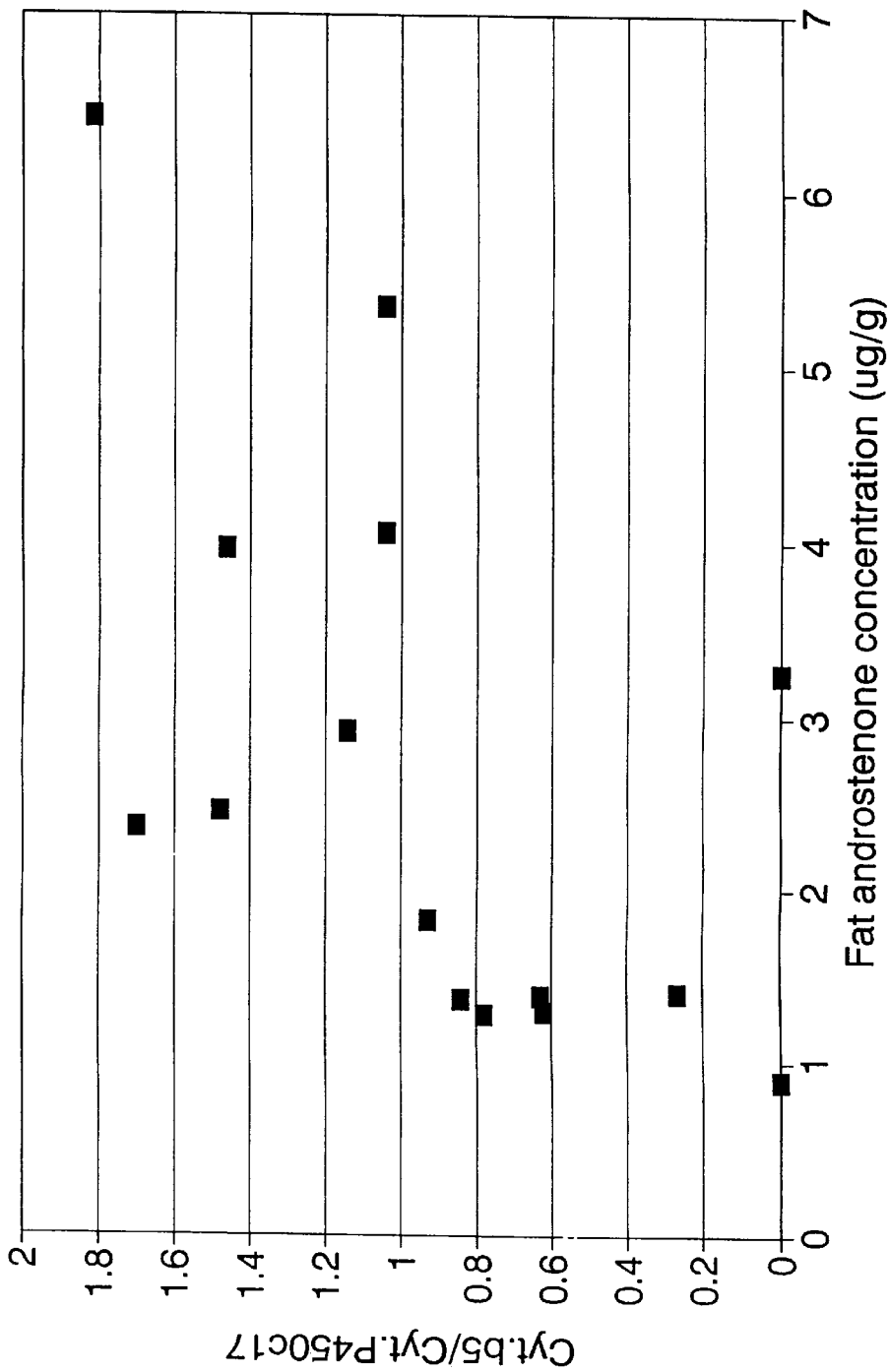
FIG. 1. A graph showing the ratio of cytochrome b5 to cytochrome P450c17 is positively correlated to the concentration of 16-androstene steroid in fat.

The present invention relates to a method for determining if a pig is predisposed to boar taint by assaying for a low molecular weight isoform of cytochrome b5 in a sample from the pig. A low molecular weight isoform of cytochrome b5 refers to an isoform of cytochrome b5 having an approximate molecular weight of 12–14 kDa, preferably 12 kDa.

A low molecular weight isoform of b5 can be determined in a variety of samples from live pigs, or pig carcasses or parts thereof. If biochemical or immunological techniques are to be used in accordance with the invention, the sample is preferably from testis. Nucleic acids for use in the nucleic acid detection techniques of the present invention, may be obtained from source material according to established procedures such as those described in Maniatis, T., Fritsch, E. F. and Sambrook, J. Molecular Cloning, A Laboratory Manual. Cold Spring Harbour, N.Y., 1982. Source materials for nucleic acids include extracts from various body tissues or a bodily fluid such as blood, usually serum or plasma.

Before testing a sample in accordance with the methods described herein, the sample may be concentrated using techniques known in the art, such as centrifugation and filtration. For the hybridization and/or amplification-based methods described herein, nucleic acids may be extracted from a sample using techniques known in the art.

The low molecular weight isoform of cytochrome b5 can be directly or indirectly assayed using for example, the biochemical, immunological, or nucleic acid based techniques described herein.

Biochemical Methods

The low molecular weight isoform of cytochrome b5 can be isolated in a sample, in particular a testis sample, using methods based on the properties of the isoform. For example, the isoform may be detected based on size. In particular, rapid high-performance reversed phase liquid chromatographic methods, GC-MS methods, hydrophobic chromatography using a butyl-Toyopearl 650 column, successive chromatography on DEAE-cellulose, Bio-Gel P-60, and DEAE-Sephadex, and/or gel electrophoresis may be used to isolate the isoform. The isoform may be selectively detected using for example, fluorescence.

The low molecular weight isoform of cytochrome b5 may be assayed in a sample by (a) reacting the sample with cytochrome P450c17, and a substrate which is converted to a 16-androstene steroid in the presence of cytochrome P450c17, under conditions which permit the formation of a 16-androstene steroid; (b) measuring the amount of 16-androstene steroids produced in (a); and (c) comparing the amount of 16-androstene steroids with an amount produces in a control with a known concentration of the isoform. The substrate may be labelled with a detectable substance as described herein to facilitate measurement of the 16-androstene steroids. The reaction in (a) is preferably carried out at 37° C. in the presence of NADH and NADPH. 16-androstene steroids are isolated and measured using conventional techniques. In a preferred embodiment, the substrate is pregnenolone, and the 16-androstene steroid formed is 5,16-androstadien-3β-ol.

Immunological Methods

Antibodies specifically reactive with the low molecular weight isoform of cytochrome b5, including enzyme conjugates or labeled derivatives, may be used to detect low molecular weight cytochrome b5 in various samples such as testis; for example they may be used in any known immunoassays which rely on the binding interaction between an antigenic determinant of the low molecular weight isoform of cytochrome b5, and the antibodies. Examples of such assays are radioimmunoassays, enzyme immunoassays (e.g.ELISA), immunofluorescence, immunoprecipitation, latex agglutination, hemagglutination, and histochemical tests. Thus, the antibodies may be used to detect and quantify the low molecular weight isoform of cytochrome b5 in a sample. In an embodiment of the invention, the low molecular weight isoform of cytochrome b5 is detected by Western blots of testis.

Antibodies specific for the low molecular weight isoform of cytochrome b5 may be prepared using conventional methods. To prepare polyclonal antibodies, a mammal (such as a rabbit or mouse) may be immunized with the isoform, or a fragment specific to the isoform. The immunogenicity of the protein or protein fragment may be enhanced by adding an adjuvant to the protein and/or coupling the protein to an immunogenic carrier. Adjuvants include Freund's adjuvant (complete or incomplete), and tetanus toxin. Immunogenic carriers include keyhole limpet hemocyanin (KLH) and bovine serum albumin (BSA). The mammal may be immunized several times. Routes of administration include intravenous, intraperitoneal and intramuscular injections. Sera or ascites fluid obtained form the immunized animal may be used as a source of polyclonal antibodies.

To prepare monoclonal antibodies, lymphocytes may be harvested from a mammal immunized as described above. The lymphocytes may be fused with myeloma cells to prepare hybridoma cells secreting monoclonal antibodies. A hybridoma cell secreting an antibody with the appropriate affinity and avidity for the cytochrome b5 protein may be selected and cloned. The techniques for preparing monoclonal antibodies and for selecting clones are well described in the literature (Kohler and Milstein, 1975).

Other techniques may also be utilized to construct monoclonal antibodies (see William D. Huse et al., "Generation of a Large Combinational Library of the Immunoglobulin Repertoire in Phage Lambda," Science 246:1275–1281, December 1989; see also L. Sastry et al., "Cloning of the Immunological Repertoire in *Escherichia coli* for Generation of Monoclonal Catalytic Antibodies: Construction of a Heavy Chain Variable Region-Specific cDNA Library," Proc. Natl. Acad. Sci. USA 86:5728–5732, August 1989; see also Michelle Alting-Mees et al., "Monoclonal Antibody Expression Libraries: A Rapid Alternative to Hybridomas," Strategies in Molecular Biology 3:1–9, January 1990; these references describe a commercial system available from Stratacyte, La Jolla, Calif., which enables the production of antibodies through recombinant techniques). Similarly, binding partners may also be constructed utilizing recombinant DNA techniques to incorporate the variable regions of a gene which encodes a specifically binding antibody.

Enzyme conjugates or labeled derivatives of the antibodies specific for the low molecular weight isoform of cytochrome b5 may be used in the methods of the invention. Generally, an antibody of the invention may be labelled or conjugated with a substance including various enzymes, biotin, fluorescent materials, luminescent materials, and radioactive materials. Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine $I^{125}$, $I^{131}$ or tritium.

Indirect methods may also be employed in which the primary antigen-antibody reaction is amplified by the introduction of a second antibody, having specificity for the antibody reactive against the isoform.

Nucleic Acid Based Methods

The low molecular weight isoform of cytochrome b5 may be detected by screening for nucleic acid molecules (i.e. DNA) encoding the isoform in conventional hybridization methods. Nucleic acid molecules encoding proteins which regulate the formation of the isoform, or which are responsible for secondary processing of RNA to mRNA for the isoform can also be detected using conventional methods.

In hybridization methods for detecting nucleic acid molecules encoding the low molecular weight isoform of cytochrome b5, suitable probes include those based on nucleic acid sequences encoding at least 6 sequential amino acid sequences from the cytochrome b5 amino acid sequence as shown in FIG. 5 and in SEQ. ID. No.:1. The nucleic acid probe may be labelled with a radioactive substance including $^{32}P$, $^{3}H$ or $^{14}C$. The probe may also be linked to an antigen that is recognizable by a labelled antibody, a fluorescent compound, biotin, a luminescent compound, an enzyme, or an antibody that is specific for a labelled antigen. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al., 1989.

A nucleic acid molecule encoding a low molecular weight isoform of cytochrome b5 can also be isolated in a sample by selectively amplifying a nucleic acid encoding the isoform using the polymerase chain reaction (PCR) methods. It is possible to design synthetic oligonucleotide primers from the nucleotide sequence shown in SEQ ID NO:1 for FIG. 5 for use in PCR. A nucleic acid molecule encoding an isoform can be amplified in a sample using these oligonucleotide primers and standard PCR amplification techniques (see for example, Innis et al, Academic Press, 1990 and U.S. Pat. No. 4,800,159).

Amplified products can be isolated and distinguished based on their respective sizes using techniques known in the art. For example, after amplification, the nucleic acid sample can be separated on an agarose gel and visualized, after staining with ethidium bromide, under ultra violet (UV) light. The nucleic acid molecule may be amplified to a desired level and a further extension reaction may be performed to incorporate nucleotide derivatives having detectable markers such as radioactive labelled or biotin labelled nucleoside triphosphates. The detectable markers may be analyzed by restriction and electrophoretic separation or other techniques known in the art.

The conditions which may be employed in methods using PCR are those which permit hybridization and amplification reactions to proceed in the presence of a nucleic acid molecule in a sample and appropriate complementary hybridization primers. Conditions suitable for the polymerase chain reaction are generally known in the art.

Methods for Preventing Boar Taint

The finding of a correlation between the low molecular weight form of cytochrome b5 and 16-androstene steroids in pigs indicates that a substance that affects the low molecular weight isoform of cytochrome b5 will be used in preventing boar taint. Substances that specifically interact with the low molecular weight form of b5 should inhibit boar taint specifically. Substances that interact with the low molecular weight isoform of cytochrome b5 can include (a) substances that inhibit the activity of the enzyme and (b) substances that inhibit the expression of the gene encoding the enzyme. Accordingly, the present invention provides a method for preventing boar taint in a pig comprising administering to a pig one or more of the following: (a) a substance which inhibits the activity of a low molecular weight isoform of cytochrome b5; or (b) a substance which inhibits the expression of a gene encoding a low molecular weight isoform of cytochrome b5. Substances which inhibit the activity of a low molecular weight isoform of cytochrome b5 include antibodies of the isoform. Antibodies may be prepared using techniques known in the art and as described herein. Substances that inhibit the expression of a gene encoding the low molecular isoform of cytochrome b5 include antisense nucleotides that are complimentary to the nucleic acid sequence of the low molecular weight isoform. The antisense nucleotides may be constructed using chemical synthesis and enzymatic ligation reactions using procedures known in the art.

The invention provides methods for identifying substances which directly or indirectly affect a low molecular weight form of cytochrome b5 and therefore are useful in the prevention of boar taint. In an embodiment of the invention a method is provided for screening for a substance for use in the prevention of boar taint comprising:

(a) reacting cytochrome P450c17, and a low molecular weight form of cytochrome b5, and a substrate which is converted to a 16-androstene steroid in the presence of cytochrome P450c17, and at least one test substance, under conditions which permit the formation of a 16-androstene steroid;

(b) comparing the amount of 16-androstene steroid produced in (a) with an amount produced in a control reaction absent the test substance; and (c) identifying a test substance which results in a lower amount of 16-androstene steroid and thereby can be used in the prevention of boar taint.

The substrate may be labelled with a detectable substance as described herein to facilitate measurement of the 16-androstene steroid. The reaction in step (a) is preferably carried out at 37° C. in the presence of NADH and NADPH. The 16-androstene steroid is isolated and measured using conventional techniques. In a preferred embodiment, the substrate is pregnenolone, and the 16-androstene steroid formed is 5,16-androstadien-3β-ol.

The substances identified using the methods described herein or a known substance such as an antibody specific for the low molecular weight isoform of cytochrome b5, or an antisense nucleic acid molecule may be used to prevent boar taint in a pig. An antisense nucleic acid molecule is a sequence encoding the isoform inverted relative to its normal presentation for transcription. An antisense nucleic acid molecule may be constructed using chemical synthesis and enzymatic ligation reactions using procedures known in the art. Therefore, a method is contemplated for preventing boar taint in a pig comprising administering an amount of a substance which affects a low molecular weight isoform of cytochrome b5 such that it reduces 16-androstene steroid concentrations in the fat of the pig.

The substances may be formulated into compositions for administration to subjects in a biologically compatible form suitable for administration in vivo. By "biologically compatible form suitable for administration in vivo" is meant a form of the substance to be administered in which any toxic effects are outweighed by the therapeutic effects. Administration of a therapeutically active amount of the pharmaceutical compositions of the present invention is defined as an amount effective, at dosages and for periods of time necessary to achieve the desired result. The active substance may be administered in a convenient manner such as by injection, or oral administration.

The compositions described herein can be prepared by per se known methods for the preparation of pharmaceutically acceptable compositions which can be administered to subjects, such that an effective quantity of the active substance is combined in a mixture with a pharmaceutically acceptable vehicle.

An antisense nucleic acid molecule may be directly introduced into cells or tissues in vivo using delivery vehicles such as retroviral vectors, adenoviral vectors and DNA virus vectors. They may also be introduced into cells in vivo using physical techniques such as microinjection and electroporation, or chemical methods such as coprecipitation and incorporation of DNA into liposomes. Antisense molecules may also be delivered in the form of an aerosol or by lavage. The antisense nucleic acid molecules may also be applied extracellularly such as by direct injection into cells.

The reagents suitable for applying the methods of the invention to detect a low molecular weight isoform of cytochrome b5, and to identify substances useful in preventing boar taint may be packaged into convenient kits providing the necessary materials packaged into suitable containers. The kits may also include suitable supports useful in performing the methods of the invention.

Genetic Screening

The invention still further provides a method for producing pigs which have a lower incidence of boar taint comprising selecting pigs that express low levels of the low molecular weight isoform of cytochrome b5; and breeding the selected pigs. Pigs that express low levels of the low molecular weight isoform of cytochrome b5 can be identified using biochemical, immunological, and nucleic acid techniques as described herein.

Transgenic pigs may also be prepared which produce low levels of the low molecular weight isoform of cytochrome b5. The transgenic pigs may be prepared using conventional techniques. For example, a recombinant molecule may be used to inactivate or alter the gene encoding the low molecular weight isoform of cytochrome b5, or genes encoding molecules that regulate its expression, by homologous recombination. A recombinant gene may also be engineered to contain an insertion mutation which results in low expression of the low molecular weight isoform of cytochrome b5. Such recombinant constructs may be introduced into cells such as embryonic stem cells, by a technique such as transfection, electroporation, injection, etc. Cells which show low levels of expression of the low molecular weight form a cytochrome b5 may be identified for example by Southern Blotting, Northern Blotting, or by assaying for expression of the low molecular isoform using the methods described herein. Such cells may then be fused to embryonic stem cells to generate transgenic animals expressing low levels of the low molecular weight isoform of cytochrome b5. Germline transmission of the mutation may be achieved by, for example, aggregating the embryonic stem cells with early stage embryos, such as 8 cell embryos, transferring the resulting blastocysts into recipient females in vitro, and generating germline transmission of the resulting aggregation chimeras. Such a transgenic pig may be mated with pigs having a similar phenotype i.e. producing low levels of the low molecular weight isoform of cytochrome b5, to produce animals having a low incidence of boar taint.

The following non-limiting examples are illustrative of the present invention:

EXAMPLES

Example 1

The example illustrates the correlation between the soluble isoform of cytochrome b5 with fat 16-androstene steroid concentrations in boars. The following materials and methods were used in the study described in the example.

Materials and Methods

Animals

Yorkshire cross Landrace boars were obtained from the University of Guelph Swine Research Center. Animals were slaughtered at the University of Guelph, Department of Animal and Poultry Science abattoir. Testis tissue was obtained at slaughter and snap frozen in liquid Nitrogen and stored at −70° C. until use. Tissue from 15 boars was utilized in microsomal assays, tissue from 36 boars was utilized in immunoblots probed with cytochrome b5 antibody and tissue from 26 boars used in immuoblots probed with both cytochrome b5 and cytochrome P450c17 antibodies.

Immunoblots

Testis tissue was homogenized in sample buffer [1.0% cholic acid, 0.1% SDS in phosphate buffered saline, pH 7.5]. Protein concentrations of homogenates were determined (BCA kit, Pierce Chemical Co., Rockford, Ill.). Aliquots of 40 $\mu$g protein per sample were brought up to 15 $\mu$l using sample buffer. 5× loading buffer [0.5M tris.Cl (pH 6.8), 15% glycerol, 0.5M EDTA (pH 8.0), 10% SDS, 0.05% bromophenol blue, 10 mM β-mercaptoethanol] was added to a 1× final concentration. Samples were boiled for 2 min., loaded on 16% SDS-polyacrylamide gels and electrophoresed for approximately 4 hours at 75 V. Proteins were transferred electrophoretically to supported nitrocellulose (Hybond-C super, Amersham Life Science) at 35 V. for 12 hours in transblot buffer [20% methanol, 20 mM tris, 150 mM glycine] and immunoblotted according to standard protocol (ECL Western Blotting Protocols, Amersham Life Science). Primary antibodies were polyclonal anti-human cytochrome b5 and anti-human cytochrome P450c17 (donated by Dr. Alan J. Conely, North Dakota State University, Fargo, N. Dak.) Blots were visualized using autoradiography (ECL Western blotting products, Amersham Life Science). Band intensities of autoradiographs were determined using IS-100 digital imaging system (Alpha Immunotech Corp.) Porcine membrane-bound cytochrome b5 and porcine cytochrome P450c17 were purified according to the method described by Meadus et al., 1993. Purified soluble cytochrome b5 was kindly donated by Dr. Holloway, University of Virginia, Charlottesville, Va.

Microsomal Assays

Microsomes were prepared from porcine testis tissue as described by Meadus et al., 1993. The microsomal assay consisted of testis microsomes (1.0 mg/ml), 50 mM tris, pH 7.0, 20% glycerol, [7-3H] pregnenolone (1.0 $\mu$M, 50,000 cpm), 1.0 mM NADH, 1.0 mM NADPH. The reaction was started, following preincubation of microsomes at 37° C. for 5 min., by the addition of NADH and NADPH. The reaction was stopped by extraction of the microsomal mixture with 5.0 ml of methylene chloride. The methylene chloride fraction was then blown dry using a stream of nitrogen and the steroid metabolites were dissolved in methanol for analysis via HPLC. A supelcosil™ LC-18 HPLC column (Supelco, Canada Ltd., Oakville, Ontario) was used with a mobile phase of 85% acetonitrile/15% water delivered at 1.0 ml/min. Radioactive metabolites were measured on line using a Beckman 171 Radioisotope detector by mixing the mobile phase with 1 volume of Ecolite scintillation fluid (Beckman 110B solvent delivery module, Beckman Instruments, Palo Alto, Calif.). The rate of 16-androstene steroid formation was estimated from the amount of 16-androstene steroids produced from [7-$^3$H] pregnenolone as the substrate. The rate of androgen formation was estimated from the amount of androgen produced from [7-$^3$H] pregnenolone as the substrate.

RNA Preparation

Total RNA was isolated from frozen pig testis samples and from blood stored in a guanidium-thiocyanate solution using the method described by Chomczynski and Sacchi, 1987.

Reverse Transcription Polymerase Chain Reaction (RT-PCR)

The total RNA was reverse transcribed and amplified using the Access RT-PCR kit (Promega, Wis.), containing avian mycloblastosis virus (AMV) reverse transcriptase, Tfl DNA polymerase, 25 mM MgSO$_4$, 10 mM dNTP mix, and AMV/Tfl 5× reaction buffer (Promega, Wis.), and primers 2 and 4 specific to rabbit cytochrome b5 (Giordano et al., 1994). Standard protocols were used to isolate and sequence the pig membrane bound cytochrome b5 cDNA. Based on this sequence, specific oligonucleotide primers were obtained (The Great American Gene Co., CA). Primer A: 5'-CTGCACCACAAAGTGTACGA-3'(aa 29-35) SEQ. ID. NO. 2 and primer B: 5'-GTAGAAGTGATACATCAGGGA-3+(aa 129-123) SEQ ID. NO. 3. These primers were used to RT-PCR approximately 70–100 ng of total RNA isolated from pig testis or blood. The PCR was carried out for 34 cycles of 94 C. for 1.5 min, 58 C. for 2.5 min, and 68 C. for 2 min with an M J Research thermal cycler (Watertown, Mass.). An aliquot of the PCR product was then electrophoresed on a 1.2% agarose gel, stained with ethidium bromide, and a UV image recorded using a gel print 2000i computer. The gel was then transferred onto a Duralon nitocellulose membrane (Statagene, Calif.) by Southern blotting via a descending alkaline transfer method (Schleicher and Schuell, 1992) and hybridized to a [$^{32}$P] dCTP-oligolabelled pig cytochrome b5 probe at 55° C. for 3 hours in hybridization solution [6×SSC, 0.05% Blotto]. The filter was washed twice with 2×SSC/0.5% SDS solution for 30 min. at 27° C. and 55° C. respectively, air dried, and exposed to X-ray film overnight.

Statistical Analyses

Pearson correlation coefficients were calculated using SAS (1991).

Results and Discussion

Fat 16-androstene Steroid Levels and Testis Microsomal Synthesis Rate

Boar taint intensity is highly correlated to fat 16-androstene steroid concentration which, in turn, has been proposed to be determined by an equilibrium between the rate of testicular steroid anabolism and the hepatic clearance rate (Bonneau et al., 1982a). Some variability between plasma clearance rates of 16-androstene steroids has been reported in boars following castration and hCG stimulation (Bonneau et al., 1982a,b), however a relationship between testicular 16-androstene steroid synthesis rates and fat 16-androstene steroid concentration has not been previously reported. The data show a correlation between the rate of 16-androstene steroid synthesis in testis microsomes and fat 16-androstene steroid levels (r=0.660, P<0.01) indicating that the rate of testicular 16-androstene steroidogenesis in vitro greatly influences the concentration of 16-androstene steroid in fat. The rate of androgen biosynthesis was not significantly correlated to fat 16-androstene steroid levels suggesting that androgen and 16-androstene steroid biosynthesis proceed via separate pathways in vivo.

Cytochrome b5, Cytochrome P450c17 and Fat 16-androstene Steroid Levels

Figure 2:
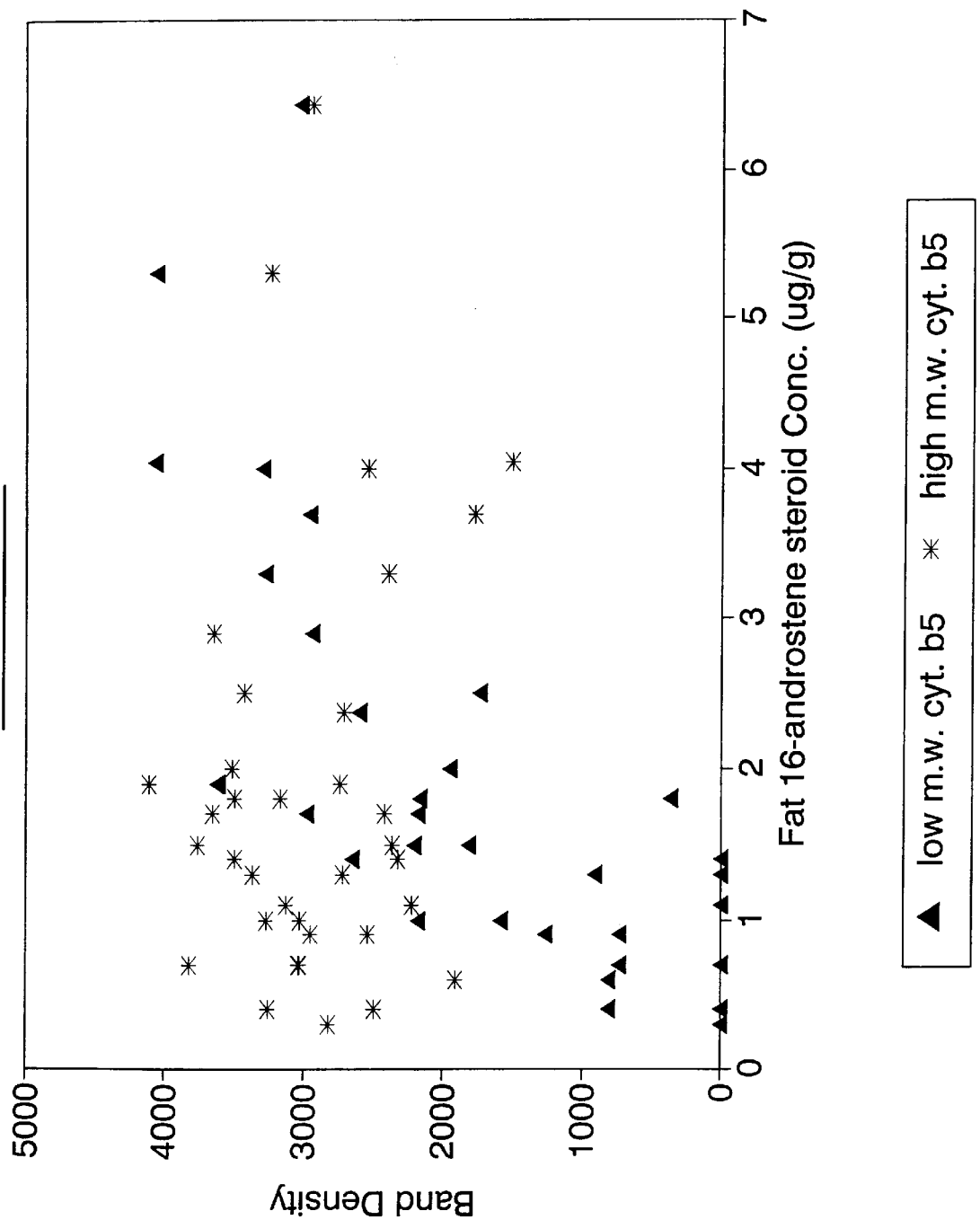
FIG. 2. A graph showing the levels of the low molecular weight isoform of cytochrome b5 are positively correlated to the concentration of 16-androstene steroid in fat.
Figure 3:
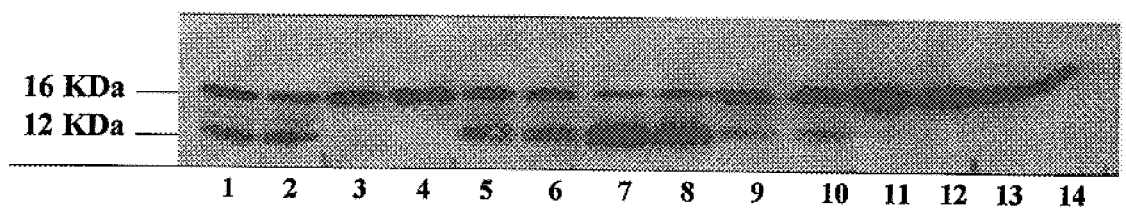
FIG. 3. Western blot. Lanes 3, 4 and 11–14 represent total testis homogenate from boars having a fat androstenone concentration less than 1.5 µg/g. The remaining lanes represent total testis homogenate from boars having a fat androstenone concentration greater than 4 µg/g.

A strong correlation was found between levels of a low molecular weight form of cytochrome b5 and fat 16-androstene steroid concentrations (FIGS. 1, 2, 3; r=0.721, P=0.0001). Two isoforms of cytochrome b5 exist in mammals: a larger, 134 aa membrane-bound isoform and a smaller, 98 aa soluble isoform (Kimura et al., 1984; Abe et al., 1985). The soluble isoform lacks the C-terminal hydrophobic tail possessed by the membrane-bound isoform and contains only the N-terminal 98 aa catalytic domain whose sequence is identical to that of the membrane-bound isoform, except for the 98th aa which is different in the porcine isoforms (Cristiano et al., 1993).

Cytochrome b5 and cytochrome P450c17 are components of the andien-β synthase enzyme system which commits pregnenolone to the formation of 16-androstene steroids. Cytochrome P450c17 is also a component of the 17α-hydroxylase-C17,20-lyase enzyme system involved in the formation of androgens. Cytochrome b5 has been shown to stimulate both 17α-hydroxylase-C17,20-lyase and andien-β synthase activities; however, porcine cytochrome b5 has been demonstrated to be essential for andien-β synthase activity in vitro (Meadus et al., 1993; Lee-Robichaud et al., 1995). High levels of cytochrome b5 have been correlated with high levels of adrenal steroidogenesis (Sakai et al., 1993) and low levels of cytochrome b5 have been implicated in steroid deficiencies (Giordano et al., 1994). The involvement of the soluble isoform of cytochrome b5 in steroidogenesis has not previously been reported. The soluble isoform of cytochrome b5, until recently only known for its function of reducing methemoglobin in reticulocytes, was demonstrated to be involved in the biosynthesis of the sialic acid, N-glycolylneuraminic representing the first report of soluble cytochrome b5 being capable of reducing a non-heme iron protein (Kwano et al., 1994). Addition of soluble supernatant to rat testis microsomes was demonstrated to greatly stimulate 17α-hydroxlyase-C17,20-lyase activity however the activating factor(s) were not identified (Betz and Tsai, 1978). A strong correlation between the ratio of low molecular weight cytochrome b5 to cytochrome P450c17 and fat 16-androstene steroid levels was also determined (FIG. 1; r=0.747, P<0.01). Results indicate that increased levels of the low molecular weight isoform of cytochrome b5, and not of cytochrome P450c17, in porcine testis are primarily responsible for a higher level of 16-androstene steroid production in boar testis.

PCR Analysis of Cytochrome b5 Isoforms

The low molecular weight form of cytochrome b5 was determined to be approximately 12 kDa by SDS-PAGE and comigrated with purified soluble cytochrome b5. The tryptic fragment of the membrane-bound isoform of cytochrome b5 has a molecular weight of approximately 12 kDa rendering it indistinguishable from the soluble isoform (Hulquist et al., 1974). Thus, it may be that the low molecular weight cytochrome b5 visualized in the immunoblots is a tryptic artifact of the membrane-bound isoform. RT/PCR and Souther blot analysis of porcine testis and blood using primers specific for the soluble and membrane-bound isoforms of cytochrome b5 demonstrated that mRNA for both isoforms exist in porcine testis (FIG. 3). This evidence combined with the strong correlation between the low molecular weight form of cytochrome b5 and fat 16-androstene steroid levels strongly suggest that the low molecular weight form of cytochrome b5 seen in the immunoblots is likely the soluble isoform of cytochrome b5, and not a tryptic fragment of the membrane-bound isoform.

Summary

The above-described results demonstrate that the level of testicular cytochrome b5, specifically the soluble isoform, is responsible for a higher rate of 16-androstene steroidogenesis and higher concentration of the 16-androstene steroids in fat. In order to reduce the rate of 16-androstene steroid production while maintaining normal production of androgens, animals with lower levels of soluble cytochrome b5 will need to be identified. A molecular marker may now be prepared in boars expressing high levels of soluble cytochrome b5. With such a genetic marker, a screening method could be established to select boars producing low levels of 16-androstene steroids while expressing normal levels of the anabolic androgens required for the desirable production traits of entire male pigs.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirely to the same extent as if each individual publication, patent or patent application was specifically and individually indicated to be incorporated by reference in its entirety.

Full Citations for References Referred to in the Specification

Abe, K., Kimura, S., Kizawa, R., Anan, F. K., and Y. Sugita. 1985. Amino acid sequences of cytochrome b5 from human, porcine, and bovine erythrocytes and comparison with liver microsomal cytochrome b5. J. Biochem.97:1659.

Betz, G. and P. Tsai. 1978. Stimulatory effect of soluble supernatant on hydroxylase activity of rat testis microsomes. Steroids. 32(3):389

Bonneau, M., Meusy-Dessolle, N., Léglise, P. C. and R. Claus. 1982a. Relationships between fat and plasma androstenone and plasma testosterone in fatty and lean young boars following castration. Acta. Endocrinol. 101:129

Bonneau, M., Meusy-Dessolle, N., Léglise, P. C. and R. Claus. 1982b. Relationships between fat and plasma androstenone and testosterone in fatty and lean young boars during growth and after hCG stimulation. Acta. Endocrinol. 101:119

Chomczynski, P. and N. Sacchi. 1987. Single-step method of RNA isolation by acid guanidium thiocyanate-phenol-chloroform extraction. Anal. Biochem. 163:156

Cristiano, R. J., Giordano, S. J. and A. W. Steggles. 1993. The isolation and characterization of the bovine cytochrome b5 gene, and a transcribed pseudogene. Geneomics. 17:348.

deLange, C. F. M. and E. J. Squires. 1995. Entire males vs castrates for pork production—financial benefits to the producer. In: Ontario Swine Res. Rev. ESSN Publ. No. 0842-9839. p 41 University of Guelph, Guelph, Canada Giordano, S, Kaftory, A. and A. W. Steggles. 1994. A splicing mutation in the cytochrome b5 gene from a patient with congenital methemoglobinemia. Hum. Genet. 93:568

Giordano. S. J. and Steggles, A. W. 1993. Differential expression of the MRNA's for the soluble and membrane-bound forms of rabbit cytochrome b5. Biochim. Biophys. Acta. 1172:95

Hulquist, D. and Passon, P., 1971. Catalysis of mathemoglobin reduction by erythrocyte cytochrome $b_5$ and cytochrome $b_5$ reductase. Nature New Biol. 229:252–254

Hulquist, D. E., Dean, R. T., and R. H. Douglas. 1974. Homogeneous cytochrome b5 from human erythrocytes. Biochem. Biophys. Res. Comm. 60(1):28

Kalkov, T. and Gower, D. B., 1970. The biosyntheseis of androstene-16-enes in boar testes tissue. Biochem. J. 117:535.

Kimura, S., Abe, K., and Y. Sugita. 1984. Differences in C-terminal amino acid sequences between erythrocyte and liver cytochrome b5 isolated from pig and human: evidence for two tissue-specific forms of cytochrome b5. FEBS lett. 169(2):143

Kwano, T., Kozutsumi, Y., Kawasaki, T. and A. Suzuki. 1994. Biosynthesis of N-glycolylneuraminic acid-containing glycoconjugates. J. Biol. Chem. 269:9024

Lee-Robichaud, P., Wright, J. N., Akhtar, M. E., and M. Akhtar. 1995. Modulation of the activity of human 17α-hydroxylase-17,20-lyase (CYP17) by cytochrome b5: endocrinological and mechanistic implications. Biochem. J. 308:901

Li, X. R, Giordano, S. J., Yoo, M. and Steggles, A. W. (199). The isolation and characterization of the human cytochrome b5 gene. Biochem. Biophys. Res. Comm.

Meadus, W. J., Mason, J. I. and E. J. Squires. 1993. Cytochrome P450c17 from porcine and bovine adrenal catalyses the formation of 5,16-androstadien-3β-ol from pregnenolone in the presence of cytochrome b5. J. Steroid Biochem. Molec. Biol. 46(5):565

Patterson, R. S. 1968. 5a-androst-16-en-3-one: compound respnsible for boar taint in the boar. J. Sci. Food Agric. 19:37

Sakai, Y., Yanase, T., Takayanagi, R., Nako, R., Nishi, Y., Haji, M., and H. Nawata. 1993. High expressionof cytochrome b5 in adrenocortical adenomas from patients with Cushings syndrome associated with high secretion of adrenal androgens. J. Clin. Endocrinol. Metab. 76:1286

Schliccher and Schell, 1992. Rapid downward blotting of RNA and DNA onto S and S nitrocellulose and nytran membranes. Application notes.

Squires, E. J. and Y. Lou. 1995. Levels of boar taint in purebred entire male pigs in Ontario. Ontrio Swine Res. Rev. ESSN Pub. No. 0842-9839 p. 20., University of Guelph, Guelph, Canada Squires, E. J., 1990. Studies on the suitability of a Colorimetric test for androst-16-ene steroids in the Submaxillary gland of pigs as a simple chemical test for boar taint. Can. J. Amin. Sci 70:1029–1040.

Squires, E. J., E. A., K. R. S. Fisher And G. D. Partlow, 1991. Comparison of androst-16-ene steroid levels determined by acolorimetric essay with boar taint estimated by a trained sensory panel. J. Animal Sci. 69:1092–1108

Velick, S. and Strittmatter, P. 1956. The oxidation reduction stoichiometry and potential of cytochrome $b_5$. J. Bio. Chem. 221:265–275

We claim:

1. A method for determining if a pig is predisposed to boar taint comprising assaying for a low molecular weight isoform of cytochrome b5 having an approximate molecular weight of 12 to 14 kDa in a sample from the pig wherein the presence of the low molecular weight isoform indicates that the pig is predisposed to boar taint.

2. The method according to claim 1, wherein the low molecular weight isoform of cytochrome b5 is assayed by detecting nucleic acid molecules which encode the low molecular weight isoform of cytochrome b5 or a portion thereof, wherein the presence of nucleic acid molecules that encode the low molecular weight isoform indicates that the pig is predisposed to boar taint.

3. The method according to claim 2, wherein the nucleic acid molecules are detected by contacting the sample with a nucleotide probe which hybridizes with the nucleic acid molecules to form hybridization products, and assaying for hybridization products.

4. The method according to claim 2 wherein the low molecular weight isoform of cytochrome b5 is assayed by treating the sample with primers which amplify the nucleic acid molecules, or a predetermined oligonucleotide fragment of the nucleic acid molecules, in a polymerase chain reaction to form amplified sequences under conditions which permit the formation of amplified sequences, and assaying for amplified sequences.

5. A method according to claim 1 wherein the low molecular weight isoform of cytochrome b5 is assayed using an antibody specific for the isoform.

6. A method according to claim 1 wherein the low molecular weight isoform of cytochrome b5 is assayed in a sample by (a) reacting the sample with cytochrome P450c17, and a substrate which is converted to a 16-androstene steroid in the presence of cytochrome P450c17, under conditions which permit the formation of a 16-androstene steroid;

(b) measuring the amount of 16-androstene steroids produced in (a); and (c) comparing the amount of 16-androstene steroids with an amount produced in a control with a known concentration of the isoform.

* * * * *